May 18, 1954 W. D. PLOUGH Plant Pat. 1,278
APPLE TREE
Filed Oct. 30, 1952
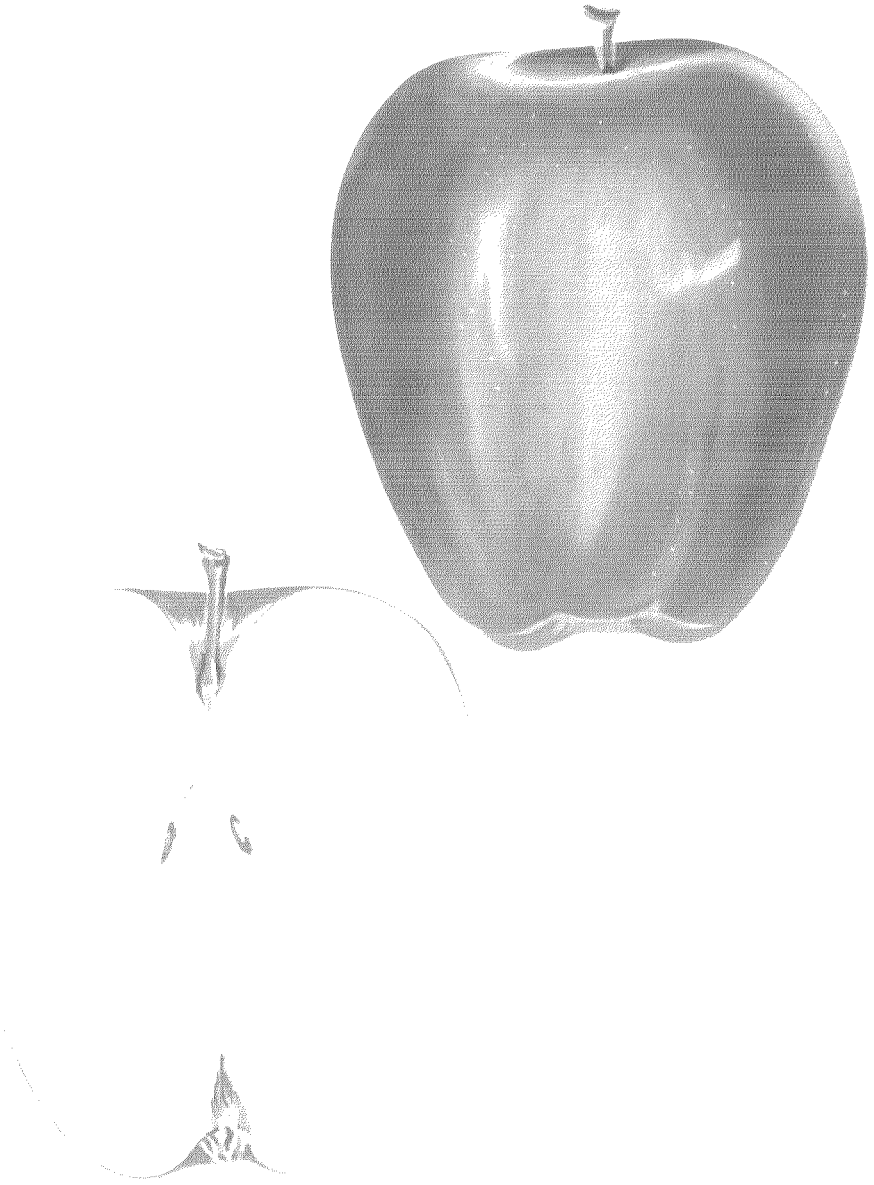
INVENTOR
Walter D. Plough
By Orville M. Kile
plant patent Agt.

Patented May 18, 1954

Plant Pat. 1,278

UNITED STATES PATENT OFFICE 1,278

APPLE TREE

Walter D. Plough, Wenatchee, Wash., assignor to Columbia & Okanogan Nursery Company, Wenatchee, Wash.

Application October 30, 1952, Serial No. 317,850

1 Claim. (Cl. 47—62)

My discovery relates to improvements in apples of the type depending on color and earliness of coloring for a portion of their commercial value.

My new variety is a bud sport of the well-known variety Richared Delicious, not patented. Richared is of the true Delicious type but colors earlier, has more bright red color, and it colors with an all-over blush rather than with a somewhat striped effect as is the case with the older Delicious. My new variety has the same appearance as Richared Delicious and appears to be almost identical with it in all respects except for its habit of coloring up approximately ten days earlier than Richared when grown under the same conditions of soil and climate.

This new variety was discovered by me in my orchards near Wenatchee, Washington, as a main limb sport on a Richared Delicious tree. When observed during the latter part of August, the fruit on the sporting limb was far more advanced in coloring than the fruit on the rest of the tree. I have reproduced it asexually by means of budding nearby apple trees where soil and climatic conditions are the same, and have carefully observed the much earlier coloring date of this new variety both on the original sporting limb and on the budded trees.

The accompanying illustration shows a typical specimen of the fruit in somewhat larger than natural size, also a cross-section showing the flesh, core, seeds, stem and other typical features. A more detailed description follows:

Tree: Rather large, vigorous and spreading in character; hardy and productive.

Fruit: Large and oblong-conic in shape, averaging about 3 inches in length and slightly less across at the widest point. Slightly ribbed, with five knob-like protrusions at the calyx end. Stem long, medium thick, and slightly pinkish in color; cavity deep, broad and sometimes furrowed; calyx medium, nearly closed; basin deep, wide, abrupt and furrowed; skin smooth, medium thick and tenaceous; core medium size; seeds plump, medium size, brown; flesh slightly yellowish, firm, tender, juicy, moderately aromatic; flavor sub-acid, very pleasant.

*Color.*—Bright, shiny red, being Carmine (Plate I, Ridgway's Color Standards and Nomenclature) in the darkest areas and shading out to approximately Eugenia Red (Plate XIII), with some lighter areas on a typical specimen. The darkest areas shown in the illustration give the artist's conception of shaded effects; the true color is more readily apparent in the central and left portions of the illustration. The color is an all-over blush, and shows no stripes as is common with Delicious (not patented), Shotwell Delicious (Plant Patent No. 90), and Starking (not patented). Small whitish dots speck the surface in considerable numbers but without forming any noticeable pattern. The inside of the cavity at the stem end is greenish.

*Coloring date.*—Approximately ten days earlier than that of Richared when grown alongside under same soil and climatic conditions and earlier than any other red Delicious variety known to me, including Shotwell Delicious (Plant Patent No. 90).

I claim:

The variety of apple tree of the "Delicious" type herein described and illustrated, characterized particularly by its earlier coloring, its brighter and lighter red color distributed as an all-over blush rather than showing stripes.

No references cited.